United States Patent
Brask

(10) Patent No.: US 11,058,915 B2
(45) Date of Patent: Jul. 13, 2021

(54) NECKPILLOW

(71) Applicant: FREBRA HOLDING AS, Rolvsøy (NO)

(72) Inventor: Bent Brask, Rolvsøy (NO)

(73) Assignee: FREBRA HOLDING AS, Rolvsøy (NO)

( * ) Notice: Subject to any disclaimer, the term of this patent is extended or adjusted under 35 U.S.C. 154(b) by 0 days.

(21) Appl. No.: 16/344,222

(22) PCT Filed: Oct. 27, 2017

(86) PCT No.: PCT/NO2017/050275
§ 371 (c)(1),
(2) Date: Apr. 23, 2019

(87) PCT Pub. No.: WO2018/080319
PCT Pub. Date: May 3, 2018

(65) Prior Publication Data
US 2019/0254911 A1 Aug. 22, 2019

(30) Foreign Application Priority Data
Oct. 27, 2016 (NO) .................................. 20161702

(51) Int. Cl.
*A63B 23/025* (2006.01)
*A63B 21/00* (2006.01)
(Continued)

(52) U.S. Cl.
CPC ......... *A63B 23/025* (2013.01); *A61H 1/0229* (2013.01); *A61H 1/0296* (2013.01);
(Continued)

(58) Field of Classification Search
CPC .. A61H 1/0296; A61H 1/0229; A61H 1/0218; A61H 1/0292; A61H 2201/169;
(Continued)

(56) References Cited

U.S. PATENT DOCUMENTS 1,314,002 A 8/1919 Lee
3,033,198 A * 5/1962 Jensen ................ A61H 1/0218
602/33
(Continued)

FOREIGN PATENT DOCUMENTS

AT 11 120 U1 5/2010
CN 201939564 U 8/2011
(Continued)

OTHER PUBLICATIONS

International Search Report (PCT/ISA/210) issued in PCT/NO2017/050275, dated Feb. 9, 2018.
Search Report issued in Norwegian Patent Application No. 20161702, dated Mar. 23, 2017.
Written Opinion (PCT/ISA/237) issued in PCT/NO2017/050275, dated Feb. 9, 2018.

*Primary Examiner* — Megan Anderson
*Assistant Examiner* — Kathleen Vermillera
(74) *Attorney, Agent, or Firm* — Birch, Stewart, Kolasch & Birch, LLP

(57) ABSTRACT

An apparatus and method for training muscle strength and mobility in the neck provides a dynamic resting position without pressure on the neck, of a person when in lying position. The apparatus includes a base element, a head support suspended floating above the base element, and a neck support rising from the base element. The neck support provides a fulcrum that defines head movement to a pivoting motion about a first axis (X) which runs sideways substantially along the shoulder line of the body, a pivot connection between the head support and the base element defines head movement to a pivoting motion about a second axis (Y) transversely to the first axis, and by its floating suspension the head support defines head movement to a pivoting motion about a third axis (Z) running in the longitudinal direction of the neck and body.

20 Claims, 3 Drawing Sheets

Figure 1:
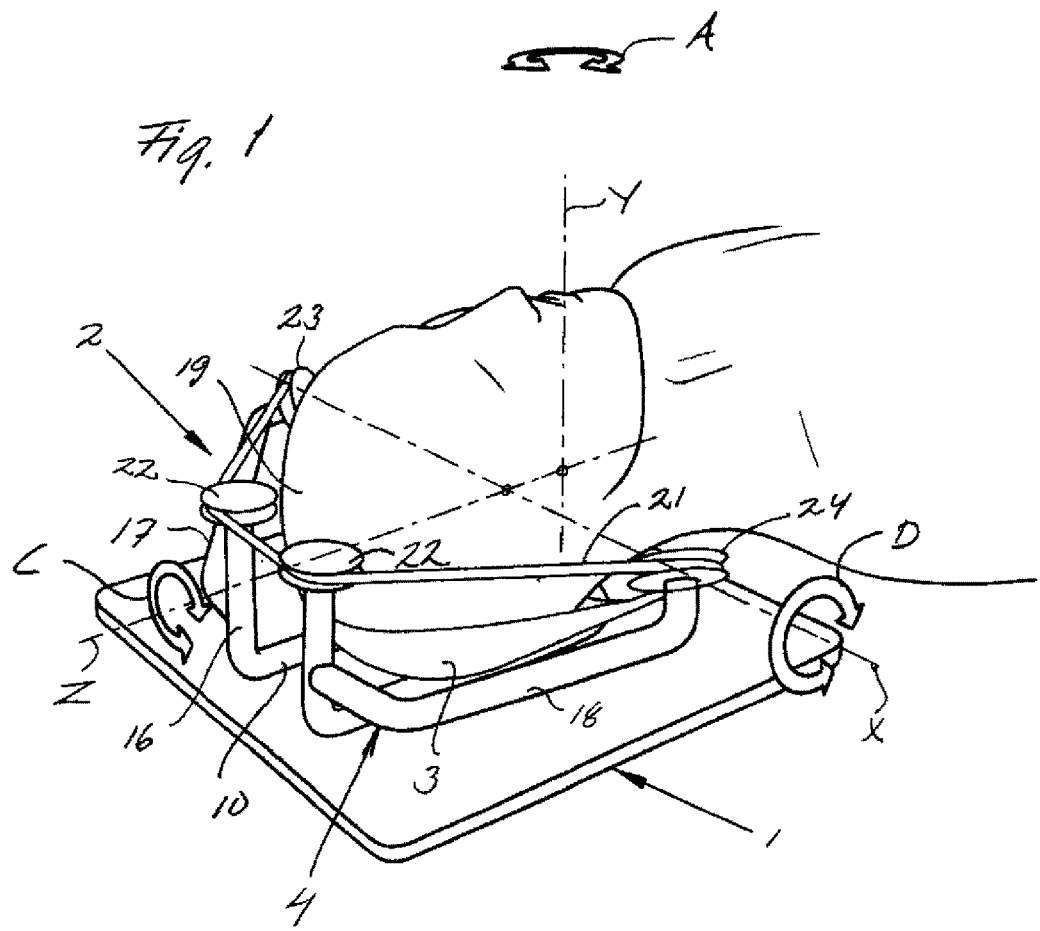

(51) Int. Cl.
*A61H 1/02* (2006.01)
*A63B 21/068* (2006.01)
*A63B 21/012* (2006.01)

(52) U.S. Cl.
CPC .. *A63B 21/00061* (2013.01); *A63B 21/00178* (2013.01); *A63B 21/154* (2013.01); *A63B 21/4003* (2015.10); *A63B 21/4047* (2015.10); *A61H 2201/1261* (2013.01); *A61H 2201/1607* (2013.01); *A61H 2201/1611* (2013.01); *A61H 2201/1664* (2013.01); *A61H 2201/1671* (2013.01); *A61H 2201/1676* (2013.01); *A61H 2203/0456* (2013.01); *A61H 2205/04* (2013.01); *A63B 21/012* (2013.01); *A63B 21/068* (2013.01); *A63B 2208/0252* (2013.01)

(58) Field of Classification Search
CPC .... A61H 2201/1661; A61H 2201/1676; A61H 2201/1671; A61H 2201/1664; A61H 2201/1261; A61H 2201/1607; A61H 2201/1611; A61H 2201/1602; A61H 2201/165; A61H 2203/0481; A61H 2203/0456; A61H 2205/04; A63B 21/4047; A63B 21/4049; A63B 21/4045; A63B 21/00178; A63B 21/4003; A63B 21/00061; A63B 21/154; A63B 21/068; A63B 21/012; A63B 23/025; A63B 2208/0285; A63B 2208/0252; A61F 5/3769; A61G 7/072; A61G 13/121; A61G 13/009; A47G 9/1009

See application file for complete search history.

(56) References Cited

U.S. PATENT DOCUMENTS

| | | | | |
|---|---|---|---|---|
| 5,336,138 | A | * | 8/1994 | Arjawat ............... A63B 23/025 482/10 |
| 5,451,202 | A | * | 9/1995 | Miller ................. A61H 1/0218 602/35 |
| 6,695,796 | B1 | * | 2/2004 | Sol mor .............. A61G 13/121 128/845 |
| 7,048,700 | B1 | | 5/2006 | Gustie |
| 8,485,195 | B2 | * | 7/2013 | River .................. A61H 1/0296 128/830 |
| 2009/0204039 | A1 | | 8/2009 | Elan et al. |
| 2010/0292051 | A1 | | 11/2010 | Benumof et al. |
| 2013/0085531 | A1 | * | 4/2013 | Hartman ............. A61H 1/0274 606/245 |
| 2014/0249461 | A1 | * | 9/2014 | Bissell ................ A61H 1/0218 602/36 |
| 2020/0054515 | A1 | * | 2/2020 | Bruesewitz ............. A61H 1/00 |

FOREIGN PATENT DOCUMENTS

| | | |
|---|---|---|
| CN | 202698623 U | 1/2013 |
| CN | 105920796 A | 9/2016 |
| DE | 20 2004 017 299 U1 | 12/2004 |
| FR | 3 005 582 A1 | 11/2014 |
| WO | WO 2013/115615 A1 | 8/2013 |
| WO | WO 2013/140406 A1 | 9/2013 |
| WO | WO 2017/052382 A1 | 3/2017 |

* cited by examiner

NECKPILLOW

TECHNICAL FIELD OF THE INVENTION

The present invention relates to an apparatus and a method for training neck muscle strength and mobility in order to improve, or restore, joint mobility in the neck of a person. It is also an apparatus that gives the neck and head a way to rest and relax.

BACKGROUND AND PRIOR ART

Whiplash is the most common non-lethal injury in car accidents in the world. In 2007, 430000 people made an insurance claim for whiplash in the UK alone.

The term "whiplash" is a non-medical term that describes a wide range of injuries to the neck that is usually caused by a sudden distortion of the neck associated with extension.

The severity of a whiplash injury ranges from mild pain for a few days, which is the case for most people, to severe disability. About 50% who have whiplash injuries from a car accident will have some long lasting problems.

If an injured person has symptoms lasting for more than six months after the accident, he or she is usually diagnosed with whiplash syndrome.

The method for treating people with whiplash injuries has changed a lot over the years. Earlier it was more common to treat the patients with a collar, either soft or hard.

However, research of later years has concluded that the best way of recovery is to use an active rehabilitation program including physical therapy exercises and postural modifications.

In fact, it is important to begin rehabilitation immediately to prevent future pain, and the main purpose with early rehabilitation is to reduce the risk for development of whiplash syndrome.

Current research supports that active mobilization rather than a collar results in a more rapid recovery in both the short- and long-term perspective and patients who participated in active therapy shortly after injury increased their mobilization of the neck and had significantly less pain within four weeks, than patients using a collar.

Active treatments are light repetitive exercises of the neck and they can be done either at home or under the care of a health professional.

When beginning a rehabilitation regimen, it is important to begin with slow movements, which include cervical rotation until pain threshold three to five times per day, flexing and extension of the shoulder joint by moving the arms up and down two to three times, and combining shoulder raises while inhaling and releasing the shoulder raise while exhaling.

Passive treatments such as acupuncture, massage therapy, and stimulation may sometimes be used as a complement to active exercises. Return to normal activities of daily living should be encouraged as soon as possible to maximize and expedite full recovery.

Due to these changes in the way of treating patients suffering from a whiplash injury several types of exercise equipment have been designed.

US 2010292051 A1 is an example of exercise equipment made for whiplash recovery. The equipment is a portable neck exercise apparatus. The apparatus is meant to be carried on your back. A headband connects the user's head to the apparatus. The headband is connected to a set of wires and an adjustable mechanism makes it possible to adjust the tension on the neck. The user exercises the neck by moving the head back and forth.

There are several problems and drawbacks with this solution. One problem is that the apparatus needs to be carried on the back. It is a large, heavy and bulky apparatus that can only be used while the user is standing. A further problem is that it is only possible to exercise the neck by tilting the head back and forth. This results in that the neck can only be exercised in one direction. Yet another problem is that the apparatus uses restraints to exercise the neck. This increases the danger of exercise related injuries.

Also FR 3005582 A1 describes an apparatus intended to help with the treatment of neck related injuries. Also this apparatus is meant to be carried on the back of the user. In this apparatus the back of the head rests on a support. The neck is exercised by pushing the head against the support.

The problem with this solution is much the same as with US 2010292051 A1. The apparatus can only be used while the user is standing. It is large, heavy and bulky, it only exercises the neck in one direction and it uses a restraining motion on the neck, increasing the dangers of injuries.

A problem for the whip-lash injured person is to find a way to rest his neck and head. To find a pillow that is not provoking the discomfort of the neck is often hard to find. This apparatus will provide a dynamic mobile way to support the head and not give any pressure on the neck.

SUMMARY OF THE INVENTION

The object of the present invention is to provide a new and improved neck muscles and neck mobility training apparatus and method that avoids the drawbacks related to prior art devices and methods. It also gives a way to give rest and relax for the head and neck in a dynamic way, without pressure to the neck.

The human head is universally movable through its ability to pivot about three axis located in the neck region. In a mechanical aspect, the complex mobility of the head is composed of nodding the head back and forth about a first axis X which runs sideways substantially along the shoulder line of the body, tilting the head about a second axis Y which runs transversely to the first axis from the front to the rear side of the body, and turning the head about a third axis Z which runs through the neck in the longitudinal direction of the neck and body.

The present invention is an apparatus by which a person can exercise the neck to improve the neck strength and mobility around the three axes X, Y and Z. This is achieved, not necessarily by restraining or controlling the motions of the head, but rather through an apparatus which is structured to define the pivot axes X, Y and Z so that the user can focus the training to each axis individually and thus to one individual component of the complex mobility of the head.

The object is achieved in an apparatus for training muscle strength and mobility in the neck of a person when in lying position, the apparatus comprising a base element arranged to be placed flat on a surface, a head support pivotally coupled to the base element, and a head capsule suspended floating in the head support above the base element.

A preferred embodiment comprises a neck support rising from the base element, wherein the neck support provides a fulcrum that defines head movement to a pivoting motion about a first axis (X) which runs sideways substantially along the shoulder line of the body, a pivot connection between the head support and the base element defines head movement to a pivoting motion about a second axis (Y)

transversely to the first axis, and by the floating suspension of the head capsule, the head support defines head movement to a pivoting motion about a third axis (Z) running in the longitudinal direction of the neck and body.

The present invention thus solves the problems of prior art apparatuses and meets the need for exercising neck muscles and improving mobility in the neck region while using little or no tension, by defining the movements of the head and neck to a fixed, yet dynamic, set of axis. It is therefore possible to exercise the joint mobility of the neck and the range of the motion of the head and neck around one axis of movement at a time. The apparatus is designed for use while the user is lying on a flat surface such as a floor or a firm bed. The base of the apparatus rests on the floor or bed and has a support for the neck. Further, there is a support for the head suspended above the base. This head support is suspended floating above the base to give the user full range of motion while at rest.

Preferably, the pivot connection between the head support and the base element is arranged movable in parallel with the third axis Z (longitudinal axis). This embodiment allows the head support to be moved towards the body of the user, this way facilitating a backwards nodding motion of the head and increasing the range of pivotal motion of the head around the first axis X.

The movable pivot connection between the head support and the base element can be realized in the form of a journal pin that is arranged sliding in linear guides arranged on the base element. This journal pin can either be secured in a lower side of the head support for insertion into the linear guide from above, or secured in a structural element arranged to travel in the linear guide, from which structural element the journal pin projects upwards for journaling of the head support in pivotal relation. This embodiment which provides rectilinear movability of the head support relative to the base element supports repetitive motion without leaving a vertical plane radial to the first axis X, and helps the user to isolate the head nodding exercise from head tilting and head turning components.

A spring member can be arranged for biasing the journal pin, and thus the head support, towards an initial position which provides the head a neutral position wherein the neck and head is neither bent forwards nor backwards. This embodiment adds to defining the angular range for a nodding mobility training session.

Said initial or neutral position can be determined by application of a stop member at a chosen location along the linear guide for the movable head support, this way permitting customization of the mobility-training apparatus to the individual user.

Said spring member can be realized in the form of a tension spring or a compression spring arranged for regulation of the force required to move the head support along the guide, this way providing the option of setting a load and resistance in the backwards nodding training.

In more detail, a preferred embodiment of the invention comprises a frame structure pivotally connected to the base element, the frame structure partially and symmetrically surrounding the head of the user in lying position, and a head capsule suspended from wheels that are rotationally journaled in the frame structure.

The suspension of the head support comprises a set of laterally disposed left and right side wheels journaled in the frame structure, the rotary axes of which are equally tilted towards a point of intersection above the apparatus, and at least one longitudinally disposed crown wheel journaled in the frame structure, positioned above the crown of the head of a user in lying position, wherein a length of a line runs through all wheels and wherein the head capsule is coupled to ends of the line between the side wheels.

The embodiment provides full support of the head without restricting head movements. The embodiment effectively relieves the neck muscles from the weight of the head in any exercise that involves pivoting about any axis X, Y or Z. Thus enabling low resistance, none weight bearing, exercises.

The head capsule may be realized as a dimensionally or form stable bowl shaped element adapted to receive the back of the head. The head capsule may be a moulded plastic piece or made of wood, e.g. A soft inner lining is preferably applied to the head capsule in order to provide comfort. The inner lining may be formed in a viscoelastic or memory foam material, this way permitting an adaption to individual head shapes.

Preferred embodiments of the invention include a solution for adjusting the height position of the head capsule above the base element. This can be accomplished by applying an adjustable geometry to the frame structure. For example, a riser section of the frame structure may be arranged extendable to effectuate a change in vertical distance between the side wheels and the base element. On the other hand, a spacer section of the frame structure which determines the horizontal distance between the side wheels may alternatively be arranged extendable to lift or lower the head capsule in effect of slackening or stretching the line. Yet another alternative involves length adjustment of the line itself.

The neck support may have a cushioned pillow carried in a free end of a cantilever leg, the fixed end of which is anchored in the base element. The cushioning counteracts pressure caused discomfort as the neck support serves as a fulcrum for the training motion around the first axis X.

The anchoring point of the cantilever leg is preferably arranged movable in the base element substantially in parallel with the third axis Z. This feature allows the user to adjust the location of the fulcrum on the back side of the neck. The self-supporting character of the cantilever leg and its movable attachment to the base element provide in combination a range of settings including a setting wherein the first axis X intersects with the second axis Y, as well as settings at which the axes are separated in longitudinal direction (axis Z direction).

The cantilever leg may be elastic and realized in the form of a spring member or leaf spring in order further to avoid pressure induced discomfort to the neck.

Adjustable tensioning means, such as friction brakes e.g., may be applied to the pivot connection between the head support and the base element, and/or applied to the rotary journals of the side wheels and/or the crown wheel(s) respectively. If appropriate, these tensioning means may optionally be used for regulation of resistance against pivoting of the head in training under load.

The object of the present invention is also met in a method for training muscle strength and mobility in the neck of a person in lying position, the method comprising i) arranging an apparatus with a base element (1), a head support (2) suspended floating above the base element, and a neck support (27) rising from the base element, such that the apparatus defines head movements to pivoting motion about a) a first axis (X) which runs sideways substantially along the shoulder line of the body, b) a second axis (Y) transversely to the first axis, and c) a third axis (Z) running in the longitudinal direction of the neck and body of the user in lying position, and ii) pivoting the head selectively around said axes one at a time.

The method optionally includes applying tensioning means to regulate a resistance against head pivotal motion around any axis X, Y and Z.

It will thus be appreciated that the apparatus and method of the present invention is equally useful in a rehabilitation program aiming to restore neck muscle strength and mobility for a person with a diagnosis, as well as in an athletic training program aiming for improved neck strength through load training.

The apparatus also enables a dynamic resting function where the head and neck is in a dynamical position. This means it locates itself at a point of least resistance according to the axis's involved and that it will provide relief from pressure and discomfort to the neck.

SHORT DESCRIPTION OF THE DRAWINGS

Figure 2:
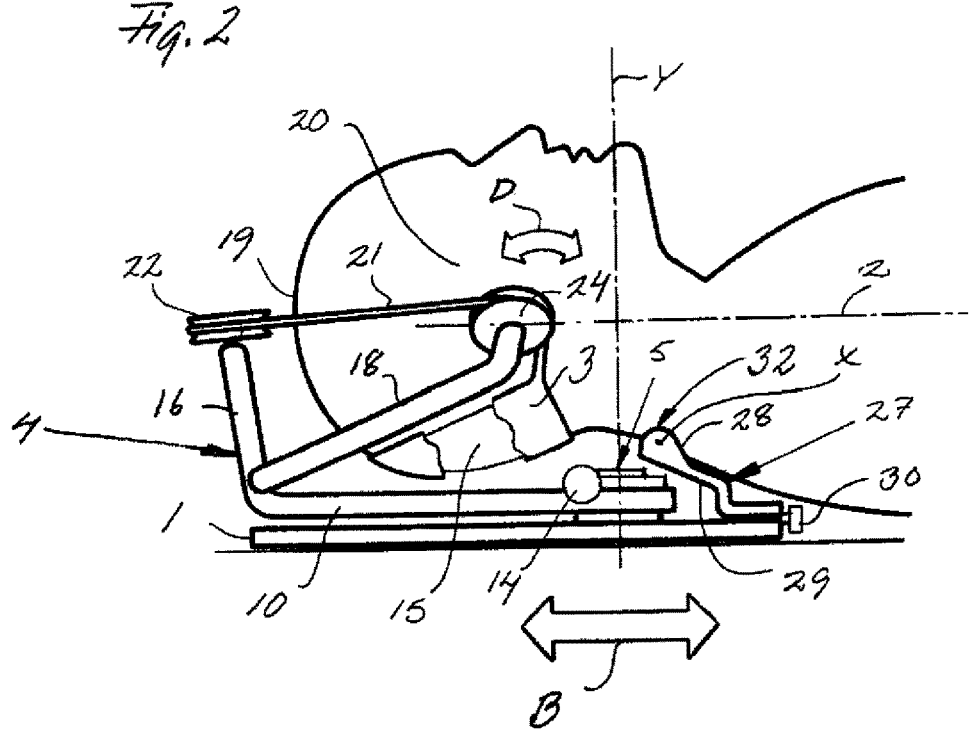
Figure 3:
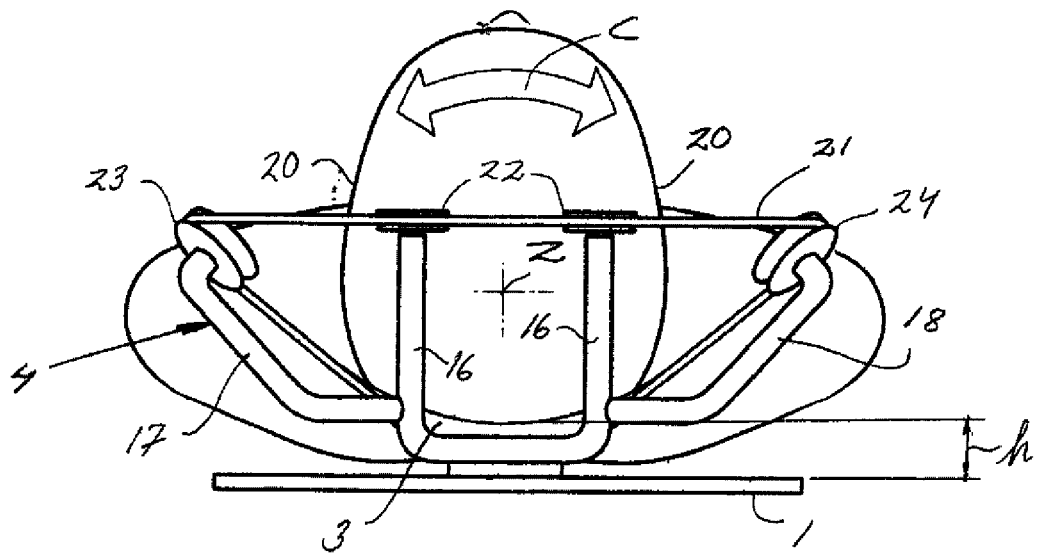
Figure 4:
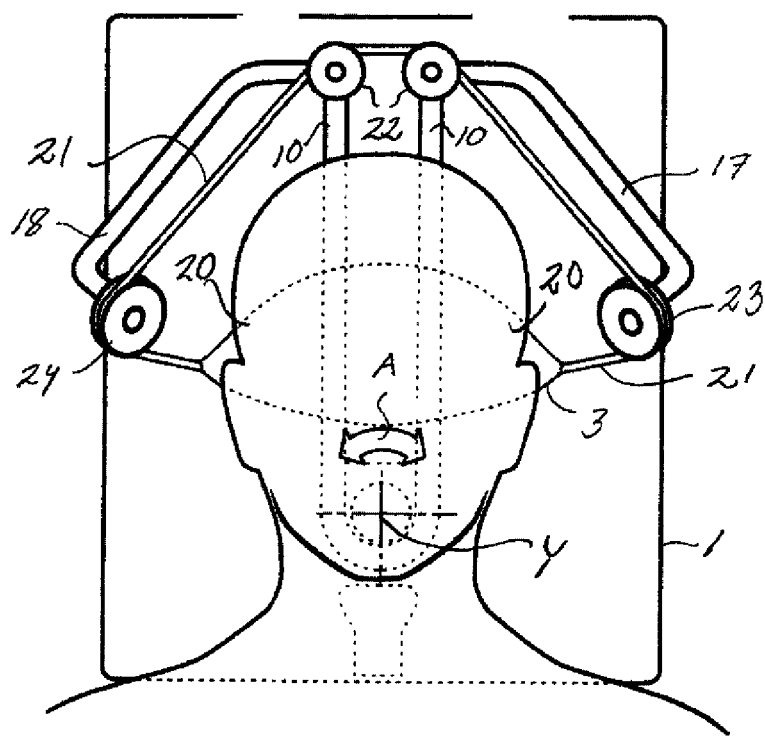
Figure 5:
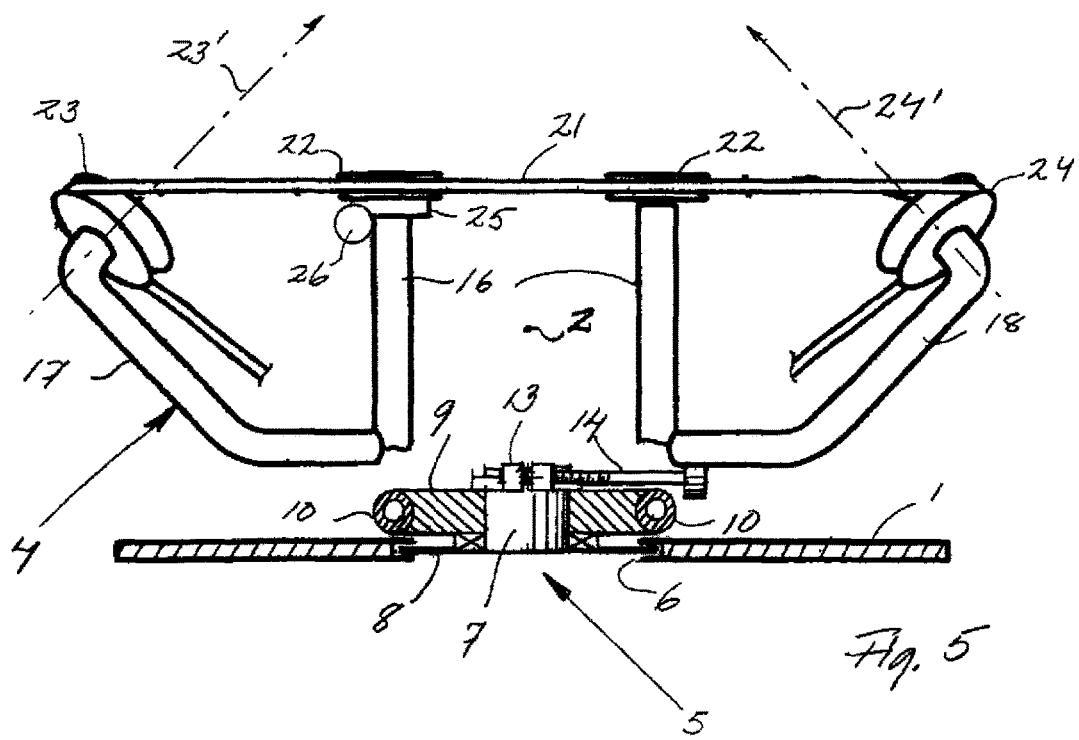
Figure 6:
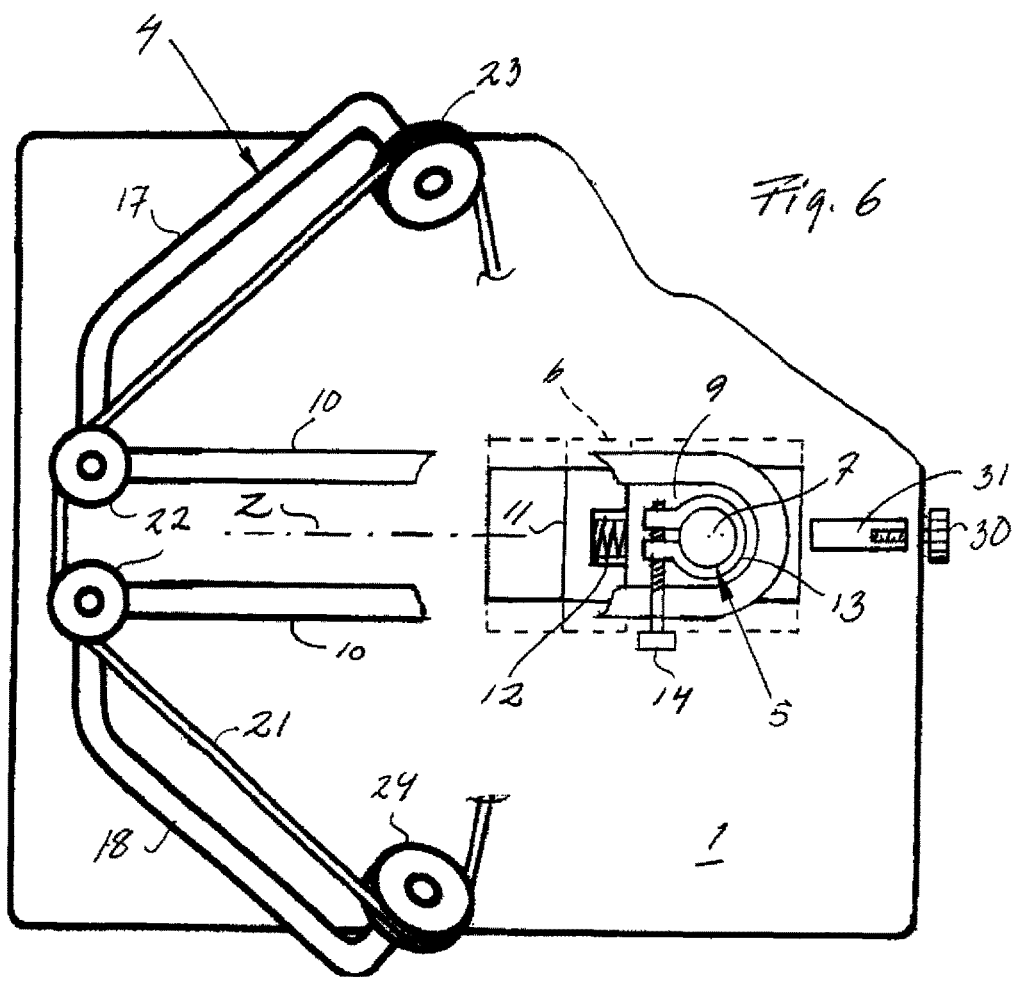

Embodiments of the invention will be further illustrated below with reference made to the accompanying schematic drawings. In the drawings, FIG. 1 is a perspective view showing an apparatus for training neck muscle strength and mobility in use by a person in lying position, FIG. 2 is a vertical plane view showing the apparatus and user as seen towards one side of the user, FIG. 3 is a vertical plane view showing the apparatus and user as seen towards the crown of head of the user, FIG. 4 is a horizontal plane view showing the apparatus and user from above, FIG. 5 is a cut out, partially sectioned view on larger scale illustrating a sliding pivot connection between interconnected basic components of the apparatus, and FIG. 6 is a partially broken away top view of the apparatus.

DETAILED DESCRIPTION OF PREFERRED EMBODIMENTS

It should initially be noted that the drawings are schematic and not true to scale. In practise, dimensions and angular relationships need to be considered and calculated from case to case. However, given the teachings presented herein, a skilled person will be able to arrive at practicable implementations of the invention using ordinary engineering skills only.

FIG. 1 illustrates in perspective the axes X, Y and Z around which pivotal motions when combined provide the complex mobility of the human head. These axes pass the neck, which in this context can be defined in general terms to include the uppermost vertebrae of the spine (not shown).

With reference to FIGS. 1-4, the basic components of an apparatus for training the mobility in the neck through pivotal motion of the head around the axes X, Y and Z are a base element 1 and a head support 2. The base element 1 is a relatively thin and flat component adapted to be placed flat on a solid surface such as a floor or a firm bed for use by a person in lying position.

The head support includes a capsule 3 which is shaped as a bowl to receive the back of the head. The head capsule is suspended in a frame structure 4 which is pivotally journaled in the base element through a pivot connection 5. The pivot connection 5 defines head pivotal motion around axis Y (see FIGS. 1 and 4: arrow A).

The head support 2 is mounted movable relative to the base element 1 substantially in the longitudinal direction as illustrated through the arrow B in FIG. 2.

As illustrated on larger scale in the cut out detail view of FIG. 5, the pivot connection 5 may be arranged sliding along a guide 6 that is formed or mounted in the base element so as to extend in parallel with the axis Z. The guide 6 may be arranged in the form of a linear groove in the base element as illustrated, or may alternatively be arranged in the form of a rail that is mounted on the top side of the base element, e.g. A journal pin 7 projects upwards from a sliding block 8 that is received to travel on the guide 6. The pin 7 projects through a bearing seat 9 which is mounted in a proximal end of a longitudinal arm section 10 of the frame structure 4.

With reference to FIG. 6, the range of movement along the linear guide 6 in the Z axis direction is determined by means of a stopping member 11. The stopping member can be arranged to be arrested in the guide 6 at a chosen location in order to determine a neutral position for the head support, at which the user is at rest. A tension spring 12 may be arranged in the stopping member and dimensioned for returning the head support to the neutral position in the relaxing sequence of a nodding exercise of the neck. The tension spring 12 can optionally be arranged adjustable and dimensioned to provide a training load and resistance against backwards nodding motion.

A split clamp 13 with tightening screw 14 may optionally be arranged as a form of frictional brake surrounding an upper end of the journal pin 7 that projects above the seat 9.

The head capsule 3 may be formed in a ductile material which accommodates to the shape of the head, such as fabric. The head capsule 3 may optionally be formed in a mouldable and form stable material such as plastic. In FIG. 2 a portion of the head capsule 3 is broken away to illustrate an inner lining 15 that is applied to provide user comfort in combination with a bowl-shaped head capsule produced in stiff material. The inner lining 15 may be formed in a material that adopts to the shape of the head, such as memory foam or a viscoelastic material.

The floating suspension of the head capsule 3 in the frame structure 4 will now be explained with reference to FIGS. 1-4. In this context, a "floating" suspension of the head support 2 with the head capsule 3 shall be understood as a suspension which provides full support of the user's head while at rest and yet permits free and full range pivoting of the head around the axes X, Y and Z.

The frame structure 4 comprises a longitudinal arm section 10, a riser section 16 adjoining a distal end of the arm section 10, and left and right wing sections 17 and 18 extending laterally from the riser section 16. The riser section 16 rises above the crown 19 of a head of a user in lying position. The wing sections 17, 18 extend on each side of the head substantially to the region of the left and right temples 20 of the head of a user in lying position. The frame structure 4 thus symmetrically and partially embraces a head that rests in the head capsule.

The head capsule 3 is suspended in a length of line 21, such as a length of a rope, a wire, or a belt or cord, which is guided through a set of pulleys or wheels that are rotationally journaled in the frame structure. The line 21 may have an oval, circular or V-shaped section to mate with the profile of the wheel peripheries.

The set of wheels includes at least one crown wheel 22 carried on the riser section 16, and left and right side wheels 23 and 24 carried on the wing sections 17 and 18 respectively. The side wheels 23, 24 are tilted at an angle that guides the line 21 in a path that goes beneath the back of the head, where the head capsule is attached to the line, i.e. to the ends of the line between the side wheels 23 and 24. The tilting angle of the side wheels is such that their journaling axes 23' and 24' intersect above the apparatus (see FIG. 5).

Basically, the wheels 22-24 are journaled on bearings to provide low friction and low resistance against rotation of the wheels. The head capsule 3 and line 21 form together an endless element journaled on wheels, such that the head capsule can be moved effortlessly from side to side between the side wheels 23 and 24 as the user turns the head in pivotal motion around the axis Z (see FIGS. 1 and 3: arrow C).

Optionally, a split clamp 25 with tightening screw 26 may be arranged at one or more wheel 22-24 as a form of frictional brake to provide the possibility of applying a tension and resistance against pivotal motion around axis Z (see the clamp and screw shown schematically in FIG. 5).

With reference to FIG. 2, a neck support 27 is arranged rising from the base element 1. The neck support comprises a cushioned pillow 28 carried in a free end of a cantilever leg 29. The pillow may be curved to provide comfortable accommodation of the neck. The other end of the cantilever leg 29 is anchored in the base element by means of an adjustable anchoring point. The anchoring point may be realized in the form of a tightening screw 30 that engages a threaded hole in a lug depending from the cantilever leg (lug not shown), the lug inserted in a groove 31 that is formed in the base element and serving as a guide for adjustable positioning of the neck support 27 in a direction that is parallel to the Z axis (see also FIG. 6).

The neck support provides a fulcrum 32 for pivotal motion of the head around axis X (see FIGS. 1 and 2: arrow D). The movable anchoring point 30, 31 permits shifting of the position of the fulcrum 32 relative to the neck vertebrae.

The embodiments illustrated in the drawings has a frame structure that comprises tubular arm, riser and wing sections, which are bent and assembled to a shape that provides the spatial relation between wheels which is required to permit head movements and support the head at appropriate height above the base element. It should be noted that the frame can be otherwise structured, such as shaped or moulded to a singular element that provides the corresponding support and relation between the wheels. The tubular embodiment however facilitates the provision of a modified apparatus wherein riser and/or wing sections are made extendable, such as telescopic, in order to accomplish adjustment of the height position of the head support in relation to the base element. Other possible modifications include, e.g., a movable attachment of the wing sections to the riser section, a tilting frame, a line that is adjustable in length, etc. The accompanying claims shall be understood to cover the invention including all such useful modifications, although not explicitly disclosed above and in the drawings, which can be seen as improvements of the disclosed embodiments.

The invention claimed is:

1. An apparatus for training muscle strength and mobility in a persona person's neck when in a lying position, the apparatus comprising:
    a base element configured to be placed flat on a surface;
    a head support pivotally coupled to the base element, the head support comprising:
        a frame structure pivotally connected to the base element, the frame structure being configured to partially and symmetrically surround the person's head in the lying position; and
        a head capsule suspended from a plurality of wheels rotationally journaled in the frame structure, the head capsule floating in the head support above the base element,
    wherein the plurality of wheels comprise a set of laterally disposed left and right side wheels journaled in the frame structure, a rotary axis of each of the left and right side wheels being equally tilted towards a point of intersection above the apparatus, and
    wherein the plurality of wheels further comprise at least one longitudinally disposed crown wheel journaled in the frame structure and configured to be positioned above a crown of the person's head in the lying position, and
    wherein a length of line runs through each of the plurality of wheels and the head capsule is coupled to ends of the line between the left and right side wheels.

2. The apparatus of claim 1 further comprising a neck support rising from the base element,
    wherein the neck support provides a fulcrum that is configured to define head movement to a pivoting motion about a first axis which is configured to, in use, run sideways along the person's shoulder line, a pivot connection between the head support and the base element is configured to define head movement to a pivoting motion about a second axis transversely to the first axis, and the floating of the head capsule is configured to define head movement to a pivoting motion about a third axis which is configured to, in use, run in the longitudinal direction of the person's neck and body.

3. The apparatus of claim 2, wherein the pivot connection between the head support and the base element is configured to be movable in parallel with the third axis.

4. The apparatus of claim 3, wherein the pivot connection comprises a journal pin that is configured to be in linear guides arranged on the base element.

5. The apparatus of claim 4, wherein the journal pin configured to slide in the linear guides arranged on the base element is spring-biased towards an initial position.

6. The apparatus of claim 4, wherein a height position of the head capsule above the base element is adjustable through an adjustable geometry of the frame structure.

7. The apparatus of claim 2, wherein the neck support comprises a cushioned pillow carried in a free end of a cantilever leg, a fixed end of which is anchored in the base element.

8. The apparatus of claim 7, wherein an anchoring point of the cantilever leg is movable in the base element in parallel with the third axis.

9. The apparatus of claim 7, wherein the cantilever leg is a spring member.

10. The apparatus of claim 2, wherein a height position of the head capsule above the base element is adjustable through an adjustable geometry of the frame structure.

11. The apparatus of claim 3, wherein a height position of the head capsule above the base element is adjustable through an adjustable geometry of the frame structure.

12. The apparatus of claim 1, wherein the head capsule is bowl shaped and configured to receive a back of the person's head.

13. The apparatus of claim 12, wherein the head capsule comprises a form stable element which has a soft inner lining.

14. The apparatus of claim 13, wherein the soft inner lining is a viscoelastic or memory foam material.

15. The apparatus of claim 12, wherein a height position of the head capsule above the base element is adjustable through an adjustable geometry of the frame structure.

16. The apparatus of claim 1, wherein a height position of the head capsule above the base element is adjustable through an adjustable geometry of the frame structure.

17. The apparatus of claim 1, wherein a height position of the head capsule above the base element is adjustable through length adjustment of the line.

18. The apparatus of claim 1, wherein friction brakes are applied to a pivot connection between the head support and the base element, and/or applied to a rotary journal of at least one of the left and right side wheels and/or the at least one crown wheel respectively.

19. A method for training muscle strength and mobility in a person's neck and providing a dynamic resting position without pressure on the person's neck when in a lying position, the method comprising:
arranging an apparatus with a base element, a head capsule suspended floating above the base element, and a neck support rising from the base element, such that the apparatus defines head movements to pivoting motion about:
a first axis which runs sideways along the person's shoulder line;
a second axis transversely to the first axis; and
a third axis running in the longitudinal direction of the person's neck and body in the lying position; and
pivoting the person's head selectively around said first, second, and third axes one at a time,
wherein the apparatus comprises a head support pivotally coupled to the base element, the head support comprising a frame structure configured to partially and symmetrically surround the person's head in the lying position, and the head capsule being suspended from left and right side wheels rotationally journaled in the frame structure.

20. The method of claim 19, further comprising applying a resistance against head pivotal motion around any of the first, second and third axes.

* * * * *